(12) United States Patent
Mourad et al.

(10) Patent No.: US 10,132,731 B2
(45) Date of Patent: Nov. 20, 2018

(54) LOAD FRAME TESTING DEVICE ADAPTED TO TEST DIFFERENT ENVIRONMENTAL CONDITIONS

(71) Applicant: United Arab Emirates University, Al Ain (AE)

(72) Inventors: Abdel-Hamid Ismail Mourad, Al Ain (AE); Ali Hilal Alnaqbi, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 15/839,008

(22) Filed: Dec. 12, 2017

(65) Prior Publication Data
US 2018/0100789 A1    Apr. 12, 2018

Related U.S. Application Data

(62) Division of application No. 14/942,110, filed on Nov. 16, 2015.

(51) Int. Cl.
*G01N 17/00* (2006.01)
*G01N 3/02* (2006.01)

(52) U.S. Cl.
CPC ............ *G01N 3/02* (2013.01); *G01N 17/00* (2013.01); *G01N 2203/022* (2013.01)

(58) Field of Classification Search
CPC .... G01N 3/04; G01N 2203/0435; G01N 3/08; G01N 3/16; G01N 2203/0003; G01N 2203/0037; G01N 2203/0017; G01N 2203/0067; G01N 3/02; G01N 3/20; G01N 2203/0023; G01N 2203/0042; G01N 2203/0252; G01N 2203/024; G01N 17/002; G01N 2203/0044; G01N 2203/0282; G01N 2203/0242

See application file for complete search history.

(56) References Cited

U.S. PATENT DOCUMENTS

| 3,203,232 | A | * | 8/1965 | Lehnig, Jr. | ............... G01N 3/16 100/289 |
| 5,095,757 | A | | 3/1992 | Larsen et al. | |
| 5,677,494 | A | * | 10/1997 | Keener | ................. G01N 3/307 73/760 |

(Continued)

*Primary Examiner* — Harshand R Patel
*Assistant Examiner* — Brandi N Hopkins
(74) *Attorney, Agent, or Firm* — Hayes Soloway PC

(57) ABSTRACT

A load testing system comprising a load frame device adapted to load test one or more test specimens and to generate load test measurements; one or more environment controlling chambers adapted to be positioned within the load testing frame for subjecting the one or more test specimens to desired environmental conditions; one or more environment condition regulators adapted to be connected to the one or more environment controlling chambers for regulating the desired environmental conditions; a data acquisition device for receiving sustain load measurements of the one or more test specimens and environmental condition measurements to which the one or more test specimens are subjected during the load test; and a load monitoring device adapted to be connected to the data acquisition device for receiving and monitoring the sustain load measurements and the corresponding environmental condition measurements as a function of time.

18 Claims, 8 Drawing Sheets

(56) References Cited

U.S. PATENT DOCUMENTS

| | | | |
|---|---|---|---|
| 6,938,494 B2* | 9/2005 | Takada | G01N 3/32 73/760 |
| 9,304,057 B2* | 4/2016 | Huang | G01M 5/0075 |
| 9,696,218 B2* | 7/2017 | Lemmer | G01K 13/12 |
| 2004/0144180 A1* | 7/2004 | Imamura | G01N 3/08 73/796 |
| 2009/0031820 A1* | 2/2009 | Kranzmann | G01N 3/02 73/856 |

* cited by examiner

LOAD FRAME TESTING DEVICE ADAPTED TO TEST DIFFERENT ENVIRONMENTAL CONDITIONS

FIELD OF THE DISCLOSURE

The invention relates to sustain load measurement, and more particularly to a system and device for sustain load measurement and monitoring the sustain load applied on a test specimen as a function of time and under different environmental conditions.

BACKGROUND OF THE DISCLOSURE

Load frame testing is a critical part of product design, development and manufacturing the product at large scale. The load frame testing involves subjecting a test sample to various loading and environmental conditions to evaluate how it performs in real life conditions. The test results help in determining the durability strength of a particular sample and reliability of a particular design. For this purpose, load frames need to be accurate in measuring the parameters such as amount of applied sustained load on a sample and the value of the fluid temperature.

Typically, a load frame comprises a base, pillars/columns, a moving crosshead which moves along the pillars, and mechanical means such as screws for engaging the movement of the cross head. A load cell is attached to the crosshead. The load cell is a transducer that creates electrical signals based on the force measured. The traditional systems for load frame testing employ different types of load cells such as hydraulic load cells and strain gauge load cells, where strain gauge load cells are the most commonly used in the load testing industry.

Traditional systems of load testing have limitations. Some of these limitations are that the stress and strain (load and elongation) cannot be measured and monitored as a function of time. Other limitations include a lack of adaptation to be used to test different specimens of different physical dimensions such as thickness, lengths and breadth. Also, traditional load testing systems fail to provide an appropriate physical/mechanical structure for securely fixing the test specimens. In addition, traditional load testing systems fail to measure test specimens in different environmental conditions. Another limitation is that the traditional load frame testing systems are not portable.

SUMMARY

Accordingly, there is a need for a system and device for sustain load measurement which overcomes the above mentioned drawbacks and other limitations of traditional systems.

There is a need of a load frame testing device that overcomes the disadvantages and weaknesses of existing systems. There is a need of a load frame testing device that is portable and provides accuracy in measuring the applied sustained load/stress of a test specimen material. Further, there is a need for a load frame testing device which is adapted to test a variety of test specimens with specimens of different dimensions. Furthermore, there is need for a load frame testing device which is adapted to subject test specimens to different environmental conditions while being subject to a sustained load. Furthermore, there is a need for a load frame testing device which is adapted to test at least two test specimens simultaneously. Moreover, there is also a requirement of a load frame testing device which is adapted to simultaneously measure and monitor a load applied on a test sample as a function of time and environmental conditions.

As a first aspect of the invention, there is provided a load testing system comprising:
- a load frame device adapted to load test one or more test specimens and to generate load test measurements;
- one or more environment controlling chambers adapted to be positioned within the load testing frame for subjecting the one or more test specimens to desired environmental conditions;
- one or more environment condition regulators adapted to be connected to the one or more environment controlling chambers for regulating the desired environmental conditions;
- a data acquisition device for receiving sustain load measurements of the one or more test specimens and environmental condition measurements to which the one or more test specimens are subjected during the load test;
- a load monitoring device adapted to be connected to the data acquisition device for receiving and monitoring the sustain load measurements and the corresponding environmental condition measurements as a function of time.

Preferably, the one or more test specimens are at least two test specimens.

The one or more environment controlling chambers can be at least two environment controlling chambers such that each test specimen among the at least two test specimens is subjected to different environmental conditions using respective environment controlling chambers among the at least two environment controlling chambers.

The one or more environment controlling chambers can be a single environment controlling chamber such that the at least two test specimens are subjected to the same environmental conditions using the single environment controlling chamber.

Preferably, the one or more environment controlling chambers comprise environment condition sensors adapted to detect the environmental conditions and to send the corresponding environmental condition measurements to the data acquisition device.

Preferably, the one or more environment condition regulators are adapted to be mounted within the one or more environment condition chambers respectively.

Preferably, the environmental conditions comprise temperature and substance.

Preferably, the desired environmental conditions comprise at least one of a desired substance, temperature and humidity.

The substance can be liquid or gaz.

The desired environmental conditions can comprise hot water having a specific temperature, and the environment condition regulator can comprise a heater in this case.

The desired environmental conditions can comprise cold water having a specific temperature, and the environment condition regulator can comprise a cooler in this case.

The environment condition chamber is a preferably hermetic chamber adapted to receive at least one of the one or more test specimens.

The at least one of the one or more test specimens can be a single test specimen.

Preferably, the environment condition chamber comprises a base cover having a base cover opening and a top cover having a top cover opening, where the base cover and top cover openings are adapted to receive the test specimen such that when the test specimen is mounted to the environment condition chamber, an intermediary portion of the test specimen falls inside the chamber, a first portion of the test specimen extends away from the top cover in a first direction outside the chamber and a second portion of the test specimen extends away from the base cover in a second direction opposite the first direction outside the chamber.

Preferably, the first and second portions of the test specimen are adapted to be connected to the test frame device for applying a sustain load on the test specimen.

Preferably, the test frame device comprise a first pair of jaws adapted to be engaged by a power screw and a second pair of jaws adapted to be connected to a load cell, wherein the first pair of jaws is adapted to hold and secure in place the first portion of the test specimen and the second pair of jaws is adapted to hold and secure in place the second portion of the test specimen.

Preferably, the engagement of the first pair of jaws by the power screw comprises applying a force on the first pair of jaws for stretching the test specimen along a longitudinal axis thereof for subjecting the test specimen to a desired load.

Preferably, the test specimen has physical dimensions and wherein first and second pairs of jaws are adjustable to fit the physical dimensions of the test specimen.

As a second aspect of the invention, there is provided a load frame device comprising:
 a top plate;
 a base plate; and
 one or more load testing frames, each one comprising:
  a pair of pillars supported at one end by the top plate;
  a crosshead adapted to be mounted and to move along the pair of pillars;
  a first pair of jaws adapted to be coupled to the crosshead and to hold and secure in place a first portion of a test specimen;
  a power screw adapted to be in physical contact with the crosshead through an opening in the top plate for applying a force thereon for engaging the first pair of jaws to move along the pillars;
  a base plate;
  a load cell adapted to be securely seated and coupled to the base plate; and
  a second pair of jaws adapted to be connected to the load cell such that the force applied on the second pair of jaws is transferred to the load cell for measurement.

Preferably, the one or more testing frames are at least two testing frames.

Preferably, load frame device further comprises:
 one or more environment controlling chambers adapted to be positioned within the one or more load testing frames; and
 one or more environment condition regulators adapted to be connected to the one or more environment controlling chambers for regulating desired environmental conditions.

DESCRIPTION OF THE DRAWINGS

The advantages and features of the present invention will become better understood with reference to the following detailed description taken in conjunction with the accompanying drawings, in which.

Like reference numerals refer to like parts throughout the description of several views of the drawing.

DESCRIPTION OF THE INVENTION

The exemplary embodiments described herein detail for illustrative purposes are subjected to many variations.

Figure 1:
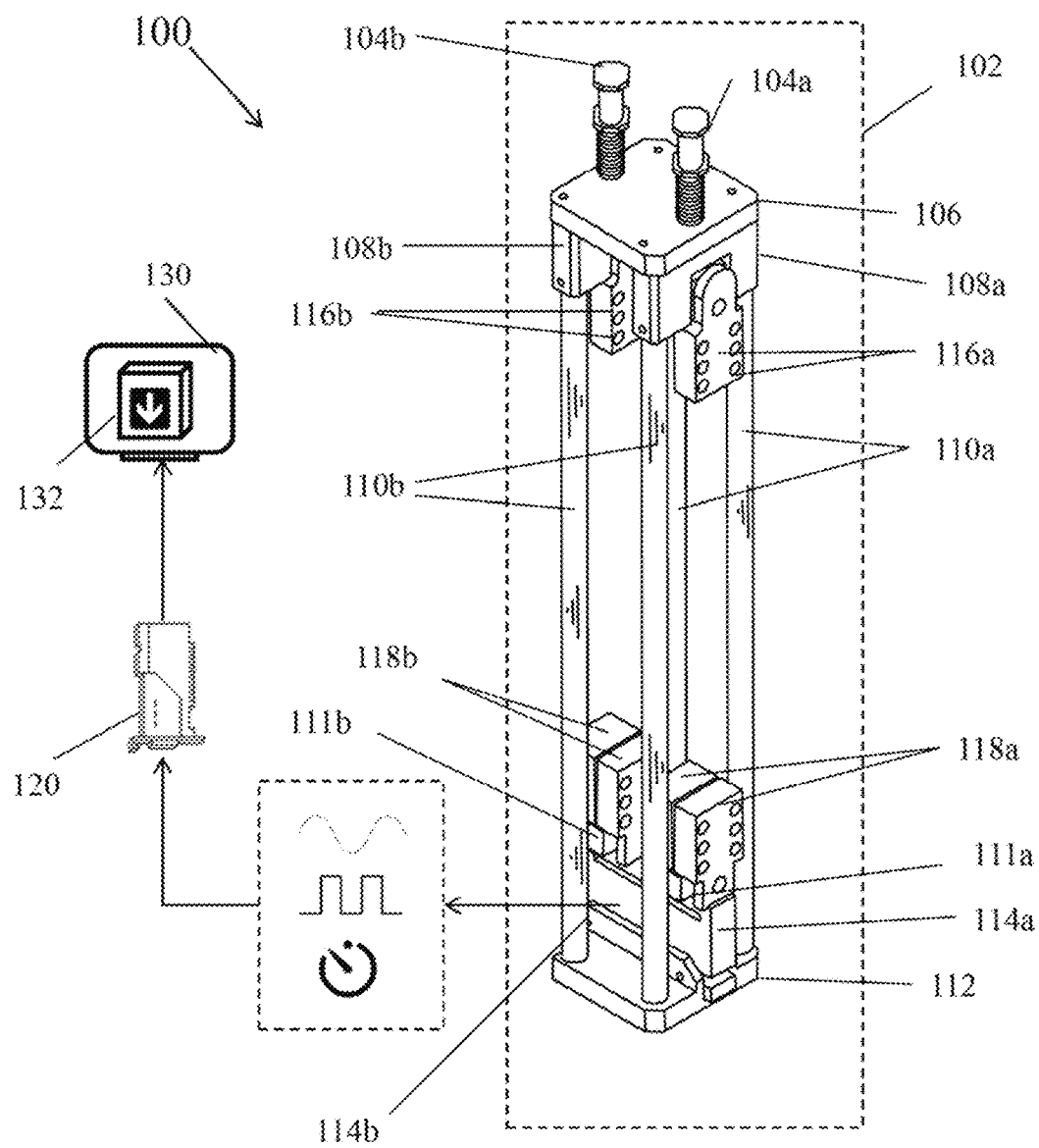
FIG. 1 illustrates a load testing system according to an embodiment of the present invention.

In an embodiment of the present invention, as illustrated in FIG. 1, there is provided a load testing system 100. The load testing system 100 comprises a load frame device 102, a data acquisition device 120 and a load monitoring device 130. The load frame device 102 is adapted to receive one or more test specimens for sustain load testing purposes.

The load frame device 102 is adapted to be connected to the data acquisition device 120 for transmitting thereto electrical signals representing the sustain load measurements of the one or more test specimens. The data acquisition device 120 is adapted to receive the electrical signals of the sustain load measurements and to convert these electrical signals into digital signals. The data acquisition device 120 is adapted to be connected to the load monitoring device 130 for transmitting thereto digital signals representing the sustain load measurements. The load monitoring device 130 comprises a microprocessor running a software 132 adapted to receive in real time and over time the sustain load measurements data and preferably to store the information inside a memory. The load monitoring device 130 is therefore adapted to receive and monitor over time the sustain load measurements of the test specimens.

Figure 2:
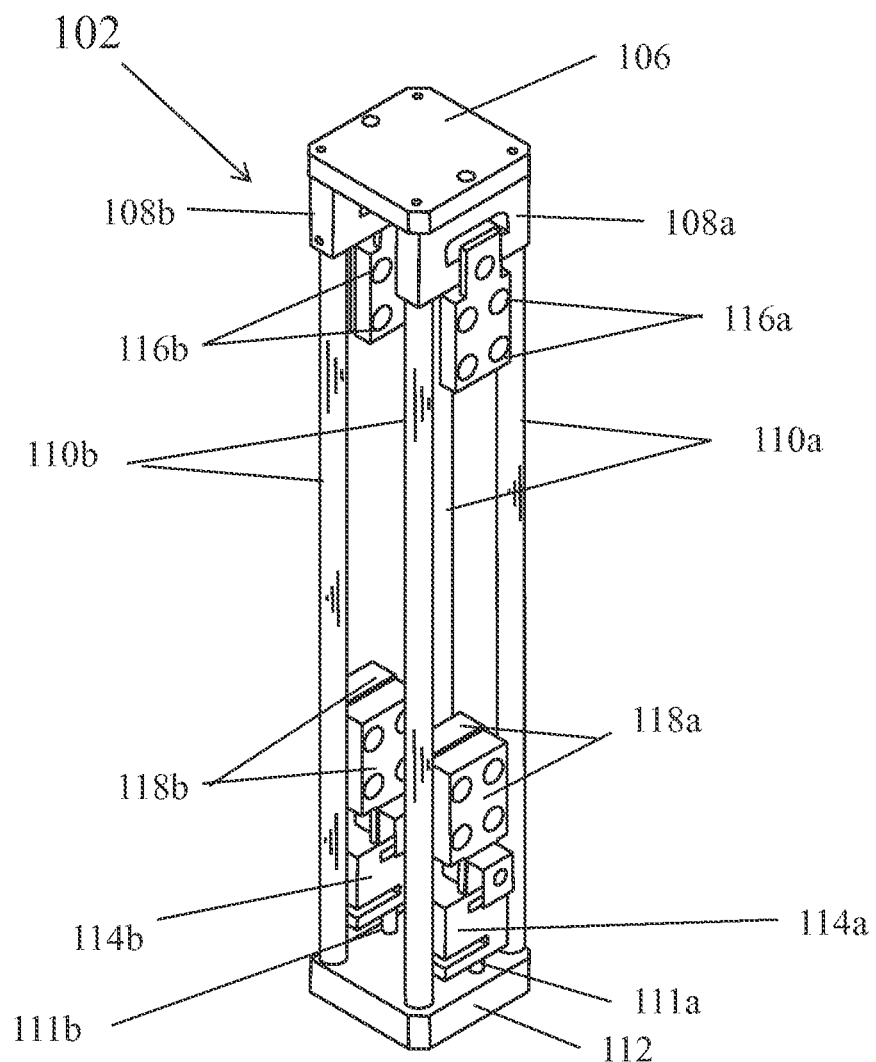
FIG. 2 illustrates a load frame device according to an embodiment of the present invention.
Figure 3:
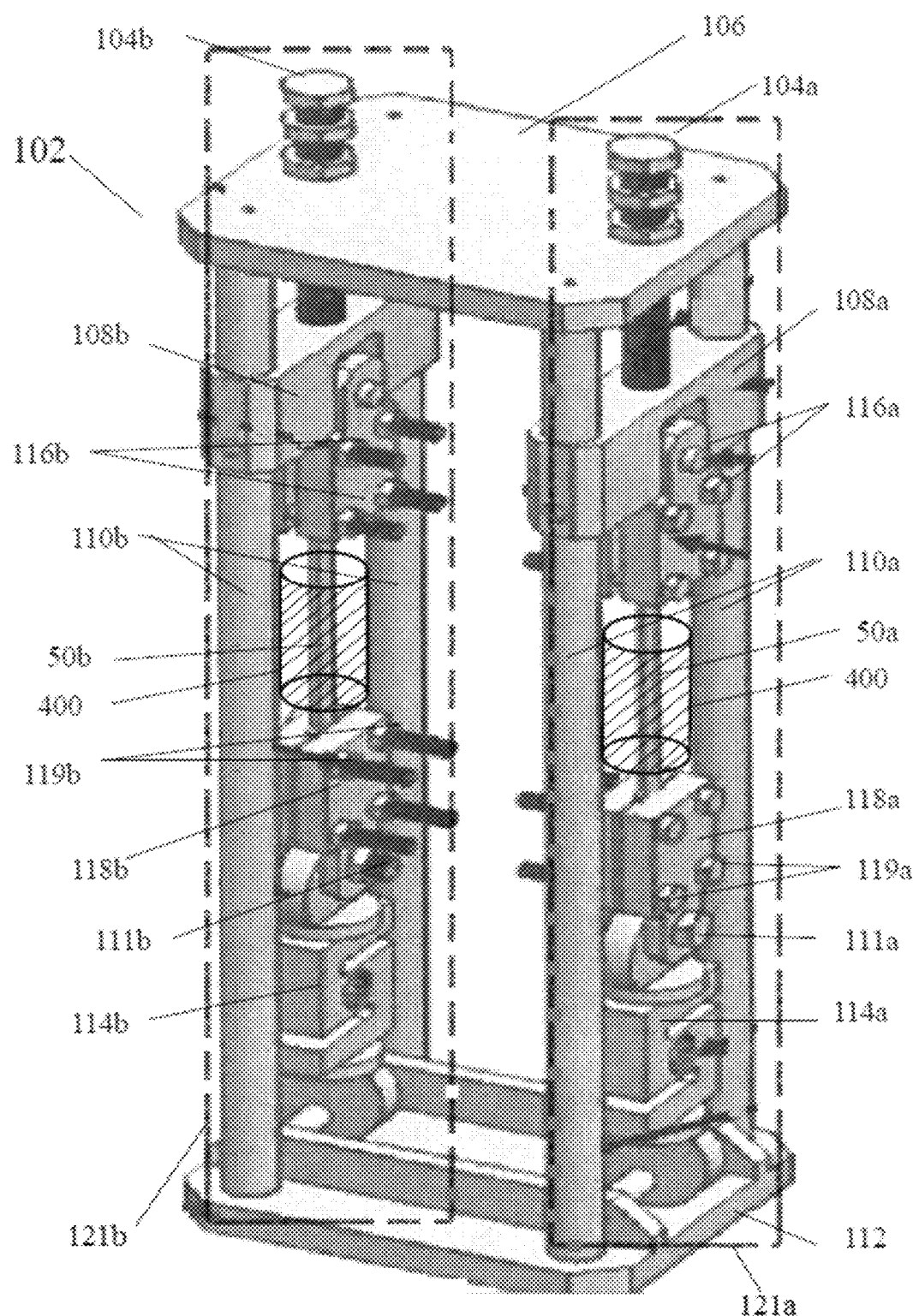
FIG. 3 illustrates a load frame device assembled with test specimens according to an embodiment of the present invention.

The load frame device 102 can be adapted to receive and test simultaneously, but independently, one or more test specimens. Referring to FIGS. 1, 2 and 3, the load frame device 102 illustrated is adapted to test simultaneously two different test specimens, which can easily be adapted to test a single test specimen or more than 2 test specimens.

In an embodiment of the present invention, the load frame device 102 comprises a top plate 106, a base plate 112, pillars 110a and 110b, upper jaws 116a and 116b, lower jaws 118a and 118b, crossheads 108a and 108b, load cells 114a and 104b and power screws 104a and 104b. The base plate 112 is adapted to receive and support load cells 114a and 114b and one end of the pillars 110a and 110b. The load cells 114a and 114b are preferably secured to the base plate 112 using eye bolts 111a and 111b respectively.

The top plate 106 is adapted to receive and support a second end of the pillars 110a and 110b. The top plate 106 comprises holes adapted to receive the power screws 104a and 104b. The cross heads 108a and 108b are respectively adapted to be coupled to the upper jaws 116a and 116b and to slide along the pillars 110a and 110b between the top plate 106 and the base plate 112 forcing the upper jaws 116a and 116b either towards or away from the lower jaws 118a and 118b.

The two test specimens 50a and 50b are respectively adapted to be placed between the upper jaws 116a and 116b and the lower jaws 118a and 118b such that when the test specimens 50a and 50b are being tested, the power screws 104a and 104b engage a force on the cross heads 108a and 108b for moving the cross heads 108a and 108b either upwardly towards the top plate 106 or downwardly towards the base 112 depending on the load desired. As the upper jaws 116a and 116b are respectively coupled to the cross heads 108a and 108b, the upper jaws 116a and 116b are forced in consequence either upwardly towards the top plate 106 or downwardly towards the lower jaws 118a and 118b. The test specimens 50a and 50b are respectively held and secured in place during the load testing between upper jaws 116a and 116b and the lower jaws 118a and 118b.

The amount of force/load applied on the one or more test specimens 50a and 50b can be controlled by controlling the extension of the screws 104a and 104b. When an increase in load is desired, the power screws 104a and 104b are screwed in forcing the upper jaws 108a and 108b away from the lower jaws 118a and 118b respectively. This results in stretching the test specimens 50a and 50b and therefore in an increase in the load applied on the test specimens. When a load decrease is desired, the power screws 104a and 104b are screwed out forcing the upper jaws 108a and 108b towards the lower jaws 118a and 118 respectively. This results in relaxing the test specimens 50a and 50b and therefore in a decrease in the load applied on the test specimens.

Each test specimen 50a/50b is tested independently of the other. Accordingly, the crosshead 108a, the upper jaws 116a, the pillars 110a, the lower jaws 118a, the load cell 114a, the eyebolt 111a and the power screw 104a form a first subframe structure 121a adapted to test a first test specimen 50a independently of a second sub-frame structure 121b comprising the crosshead 108b, the upper jaws 116b, the pillars 110b, the lower jaws 118b, the load cell 114b, the eyebolt 111b and the power screw 104b which are adapted to test a second test specimen 50b independently from the first test specimen 50a. Though, the testing of both test specimens 50a and 50b can take place simultaneously and their respective load measurements can be sent simultaneously to the data acquisition device 120. The first and second specimens 50a and 50b can have different physical dimensions, different loads, and different testing environments and can be tested in different times or alternatively at the same time.

The upper jaws 116a/116b comprise each a pair of jaws which adapted to receive therebetween and secure in place a first portion of a test specimen 50a/50b. The pair of upper jaws 116a/116b has holes 117a/117b adapted to receive bolts for fastening the pair of upper jaws 116a/116b together once the test specimen is placed in between. Each pair of the upper jaws 116a/116b is adapted receive a test specimen of any physical dimensions which is placed between the pair of jaws 116a/116b and secured in place by bolting the pair of jaws 116a/116b together using bolts inserted inside the holes 117a/117b. The same principle applies to the lower jaws 118a/118b which each also comprises a pair of jaws which work in a similar manner to the upper jaws 116a/116b.

Each pair of lower jaws 118a/118b is adapted to receive and secure in place a second portion of the corresponding test specimen 50a/50b. The lower jaws 118a/118b have holes 119a/119b adapted to receive bolts as fastening means in order to secure the test specimen 50a/50b in place. Accordingly, a first portion of a first test specimen 50a/50b is secured in place by the first pair of upper jaws 116a where a second portion of the first test specimen is secured in place by the first pair of lower jaws 118a. In a similar manner, a first portion of a second test specimen 50a/50b is secured in place by the second pair of upper jaws 116b where a second portion of the second test specimen 50a/50b is secured in place by the second pair of lower jaws 118b.

The cross head 108a/108b is controlled by a power screw 104a/104b. The load applied through the power screw 108a/108b forces the cross head 108 to move along the pillars 110a/110b. The load on the specimen can be maintained constant, increased or decreased through the power screw 104a/104b. When the power screw 104a/104b is screwed in, the crosshead 108a/108b and consequently the upper jaws 116a/116b move upwardly towards the top plate 106 and a load increases on the test specimen. When the power screw 104a/104b is screwed out, the crosshead 108a/108b and consequently the upper jaws 116a/116b move downwardly towards the base plate 112 and a load decreases on the test specimen. This mechanical arrangement to apply load on the test specimens 50a/50b can however be modified without departing of the scope of the invention.

The load cell 114a/114b is adapted to sit and to be secured in place to the base plate 112 using an eye bolt 111a/111b. The lower jaws 118a/118b are adapted to sit and to be secured in place to the load cell 114a/114b using an eye bolt 115a/115b. The load cell 114a/114b measures the force applied on the test specimen 50a/50b which is secured in place using the upper jaws 116a/116b and the lower jaws 118a/118b. For clarity purposes, the first pair of upper jaws 116a and the first pair of lower jaws 118a secure the first test specimen 50a in place, where the second pair of upper jaws 116b and the second pair of lower jaws 118b secure the second test specimen 50b in place. The first power screw 104a applies a load on the first test specimen 50a by engaging the crosshead 108a to force the first pair of upper jaws 116a upwardly towards the top plate 106, where the second power screw 104b applies a load on the second test specimen 50b by engaging the crosshead 108b to force the second pair of upper jaws 116b upwardly towards the top plate 106. The load measured by the load cell 114a/114b is converted to electric signals and transmitted to the data acquisition device 120.

The data acquisition device 120 acts as a hardware interface between the load cell 114a/114b and the load monitoring device 130. The DAS The said DAS is adapted to capture the electrical signals from the load cell 104a/104b and convert them into digital signals before being transmitted to the load monitoring device 130. The data acquisition device can be a Serial Communication Data Acquisition System (DAS), a USB DAS, a Parallel Port DAS, a Compact DAS or any other suitable type. The data acquisition device 120 according to an embodiment of the invention is a Compact DAS.

The data acquisition device 120 is adapted to be connected to the load monitoring device 130 for receiving and recording the load measurements in digital format in real time. The load monitoring device 130 is adapted to monitor the specimen testing over time. A software program 132 running on the load monitoring device 130 for decoding the load measurements received from the data acquisition device 120 and for providing a load analysis in the form of load monitoring. The load monitoring device 130 comprises a processor and preferably a monitor to display the load analysis in a graphical, textual and/or multimedia form.

Different types of load cells 104*a* and 104*b* can be used. The load frame device 102 is not restricted to the use of a specific type of load cells, such as a compression load cell, an S load cell or a bending beam cell. In a preferred embodiment, an S load cell is used. The load cell 114*a*/114*b* used in the embodiment illustrated in FIG. 1 is a bending beam load cell, where the load cell 114*a*/114*b* used in the embodiment illustrated in FIG. 2 is an S type load cell. The load frame 102 has a further advantage of load measurement with respect to measuring the minimum applied load capacity. In traditional load frame systems, the load capacity needed to test a material failure range is 30 to 40 Kilo Newton and these materials are usually subjected to sustained load in the range of 20% to 35% of their ultimate strength. But, the load capacity needed to test material failure range of different capacity to apply a sustained load in the range of 20% to 50% of the ultimate strength of composite materials.

Figure 5:
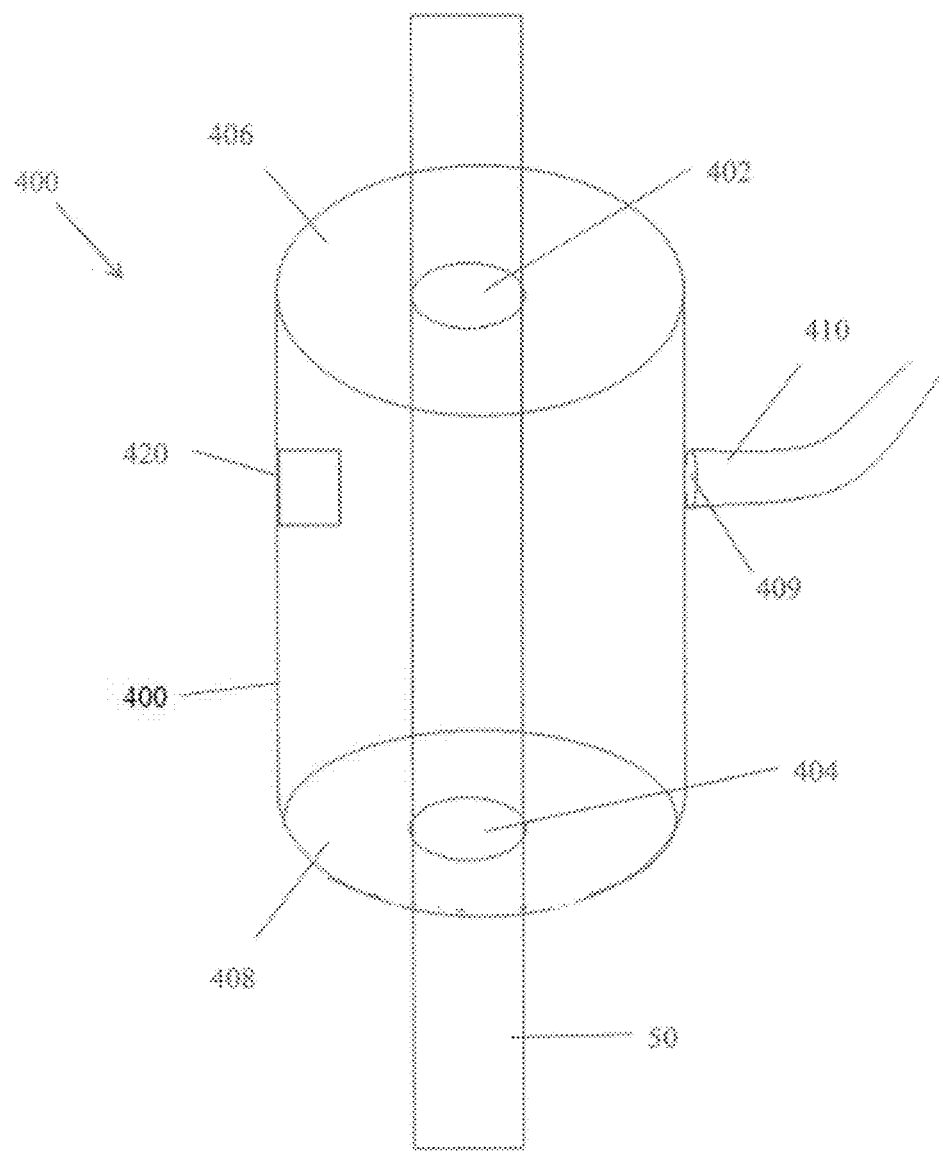
FIG. 5 illustrates an environment controlling chamber having base and top covers assembled with a test specimen according to another embodiment of the present invention.

In another embodiment of the invention, referring to FIG. 5, the load frame device 102 comprises an environment controlling chamber 400 adapted to subject the test specimen 50*a*/50*b* to different environmental conditions including but not limited to temperature and substances. The substances can be natural or chemical substances including but not limited to solvents, chemical compositions, water or any liquid or gas substances. For example, the environment controlling chamber 400 can be controlled to subject the test specimen 50*a*/50*b* to a specific temperature and/or to the interaction with a specific substance such as hot water, cold water, salty water, moisture, humidity, water vapor, gas and the like.

In an embodiment of the invention, the environment controlling chamber 400 is preferably in the form of a tube/cylinder having a base cover 408 and a top cover 406, however can take any other shape based on the suitability to be fitted within the test frame device 102. The top cover 406 has a top cover opening 402 adapted to enable a first portion of the test specimen 50*a*/50*b* to pass through upwardly towards the upper jaws 116*a*/116*b*. The base cover 408 has a base cover opening 404 adapted to enable a second portion of the test specimen 50*a*/50*b* to pass through downwardly towards the lower jaws 118*a*/118*b*. The central portion of the test specimen 50*a*/50*b* which is located between the first and second portions is therefore encompassed inside the chamber 400.

Preferably, adhesive is applied for adhering the test specimen to the base cover 408 and the top cover 406 for forming a hermetic environment controlling chamber 400 and for avoiding any leakage of substance and/or temperature from the top cover opening 402 and the base cover opening 404. The environment controlling chamber is preferably made of a composite material. The environment controlling chamber 400 comprises an input/output 409 adapted to be connected to a conveyor 410 for enabling the entry/exit of temperature and/or substance inside/outside the chamber 400. The environment controlling chamber 400 according to this embodiment is made hermetic in order to be suitable to receive both liquid and gas of any temperature without risk of leakage.

Figure 4:
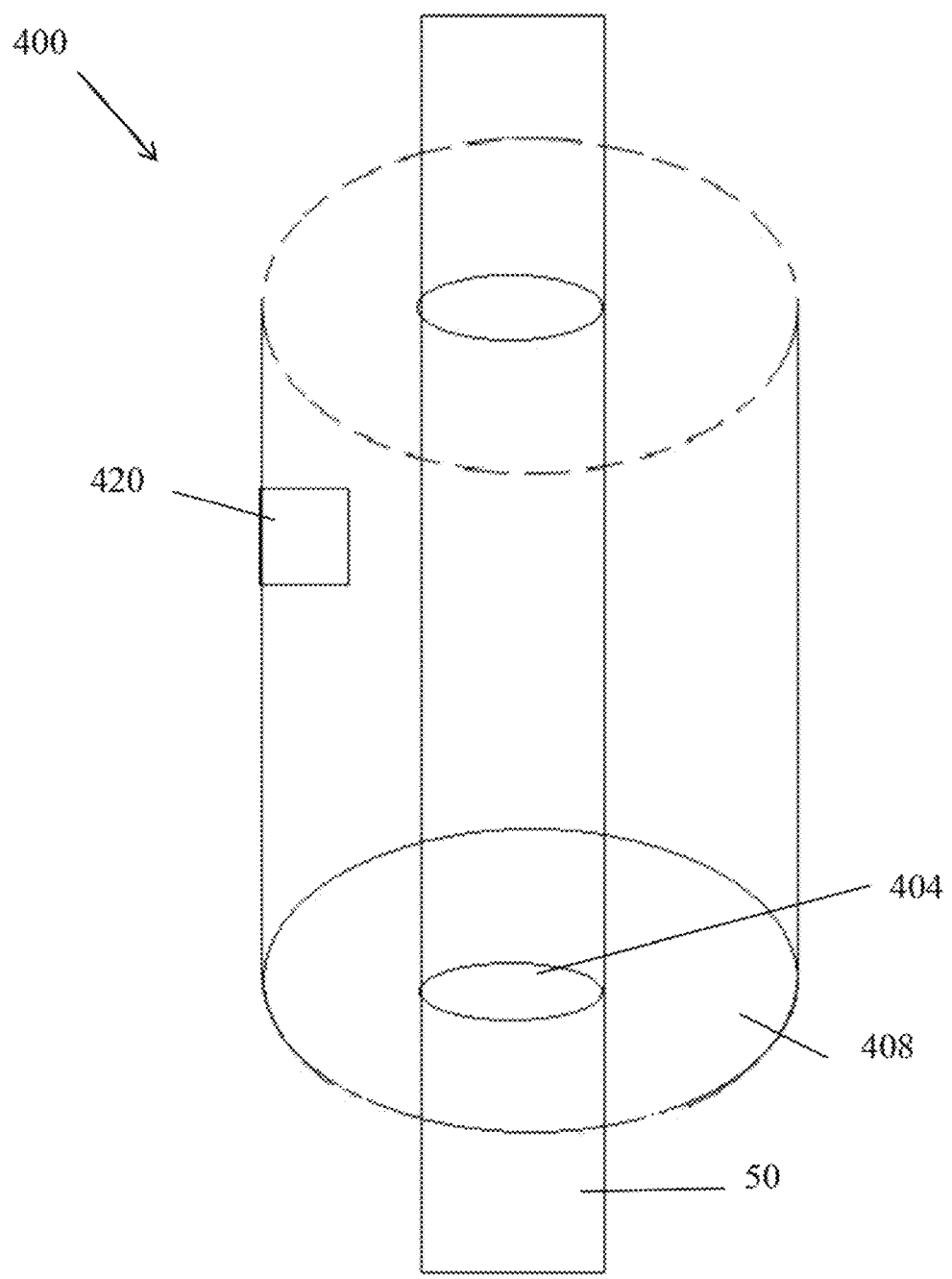
FIG. 4 illustrates an environment controlling chamber having a base cover assembled with a test specimen according to an embodiment of the present invention.

In an embodiment of the invention, referring to FIG. 4, the environment controlling chamber 400 comprises only a base cover 408 having a base cover opening 404. The top end of the chamber 400 is left open. This type of chamber can be suitable to receive liquid only such as hot or cold water. Gas may not be suitable as it may leak from the top open side.

Figure 6:
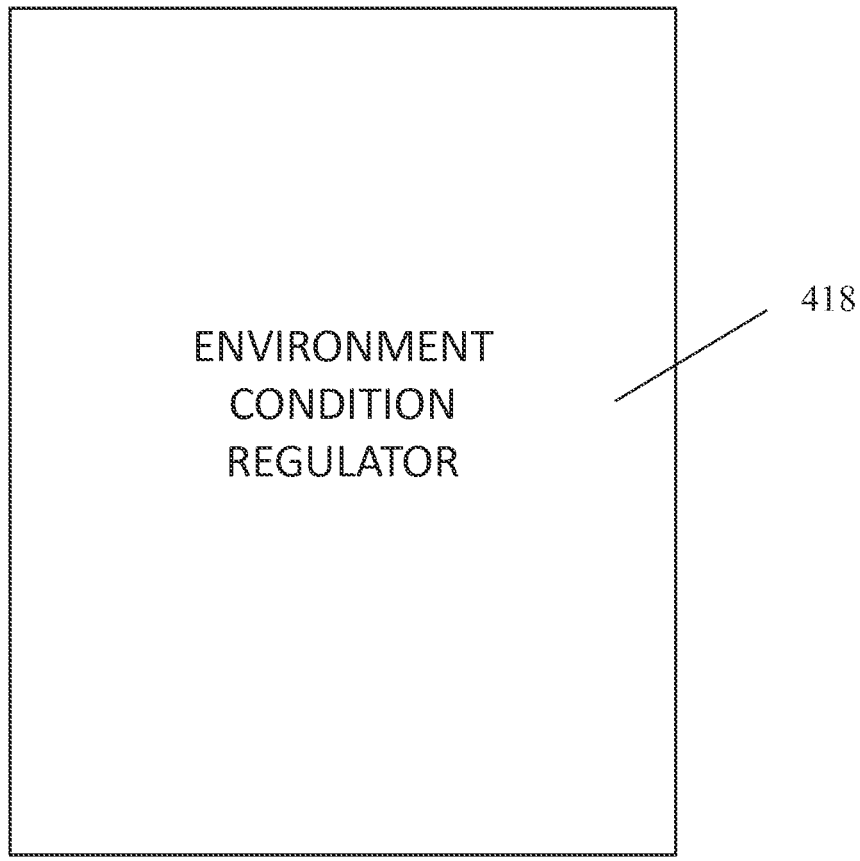
FIG. 6 illustrates an environment condition regulator according to an embodiment of the present invention.

An environment condition regulator 418 in according with an embodiment of the invention is illustrated in FIG. 6.

In an embodiment of the invention, the environment controlling chamber 400 comprises a heater for heating water when the test specimen shall be subjected to a hot water environment. In an embodiment of the invention, the heater is separate and located outside of the chamber 400 where the hot water is heated and conveyed to the chamber 400 through the conveyor 410. The conveyor 410 can be a pipe or any other type of conductor.

In an embodiment of the invention, the environment controlling chamber 400 is adapted to be secured in place between the pillars 110*a* and 110*b* of the load frame device 102 and is adapted to receive both the first and second test specimens 50*a* and 50*b* when two test specimens 50*a* and 50*b* are being tested simultaneously and subject to the same environmental conditions. In this case, the top cover 406 would comprise another top cover opening (not shown) to receive a first portion of the second test specimen 50*b* and the low cover 408 has another lower cover opening (not shown) for receiving a second portion of the second test specimen 50*b*.

In an embodiment of the invention, an independent environment controlling chamber 400 is provided for each test specimen 50*a* and 50*b*, where a first environment controlling chamber 400 is used for a first test specimen 50*a* and a second environment controlling chamber different from the first environment controlling chamber is used for a second test specimen 50*b*. In this case, the first and second test specimens 50*a* and 50*b* can be subject to different environmental conditions imposed respectively by the first and second environment controlling chambers 400.

In an embodiment of the invention, the environment controlling chamber 400 comprises sensors 420 adapted to be connected to the data acquisition device 120 for detecting and transmitting thereto environment conditions such as the temperature inside the chamber 400 and/or the concentration of substances inside the chamber such as the amount of salt, the acidity of the substance and the like. The sensors 420 can be temperature sensors, gas concentration detection sensors, substance concentration detection sensors or any other type of sensor suitable for the application used. The data acquisition device 120 is adapted to read the measurement of the sensors 420 in real time, to convert these into digital data and transmit these to the load monitoring device 130 to be recorded in association with the load measurements sent. The load monitoring device 130 receives and monitors real time load and environmental condition measurements of the test specimens and makes the required analysis as preconfigured by the computer software 132. The load measurements received and the environmental condition measurements received are as a function of time and so both the load and environmental condition measurements are associated together as a function of time.

In an embodiment of the invention, the environment controlling chamber 400 comprises a environment condition regulator 418 to regulate the environment conditions of the substance inside the chamber 400. Alternatively, the environment condition regulator 418 can be separate and outside the chamber 400 and the environment conditions of any desired substance can be first regulated using the environment condition regulator 418 and conveyed to the environment controlling chamber 400 through a conveyor 410. The environment controlling chamber 400 comprises an input/output 409 adapted to be connected to the conveyor 410. The environment controlling chamber 400 is made of a suitable material adapted to maintain and sustain the desired environment conditions during load testing conditions.

Figure 7:
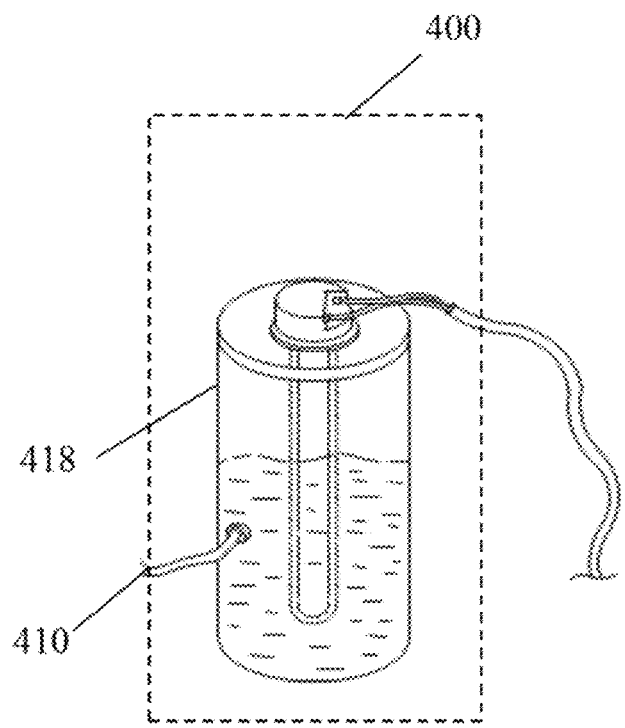
FIG. 7 illustrates a heater as an environment condition regulator according to an embodiment of the present invention.

In an embodiment of the invention, as illustrated in FIG. 7, the environment condition regulator 418 is a heater and/or a cooler depending on the application and the environmental conditions desired for the test specimen. In an embodiment, the heater is adapted to heat the substance up to 65° C. to measure the effect of moisture and temperature. In an embodiment of the invention, the environment condition regulator 418 is a humidifier adapted to create a certain level of humidity inside the environment controlling chamber 400 depending on the desired environment conditions of the test specimen 50a/50b.

In an embodiment of the invention, the environment controlling chamber 400 comprises an environment condition detection sensor 420 which is connected to a power switch for powering on the environment condition regulator 418 for regulating the environment conditions of the substance when needed based on the initial environment conditions or any changes of the environment conditions during load testing inside the environment controlling chamber 400. The environment condition detection sensor 420 can be a temperature sensor, a humidity sensor, a gas concentration sensor, a moisture detection sensor or any other type of sensors or detectors depending on the use.

In an embodiment of the invention, the environment controlling chamber 400 is adapted to fit within the load frame device 102.

Also, the e loading frame 102 is adapted to be portable and/or versatile to make it portable. In an embodiment of the invention, for example when it is not possible to have an environment controlling chamber/regulator positioned inside the load frame device 102, the portability of compact size of the device 102 are adapted to have the entire device 102 fit within a bigger environment controlling chamber/regulator such as a freezer for example to study the effect of thermal cycling or into a humidity chamber to examine the effect of the extreme environment on the test specimen.

Figure 8:
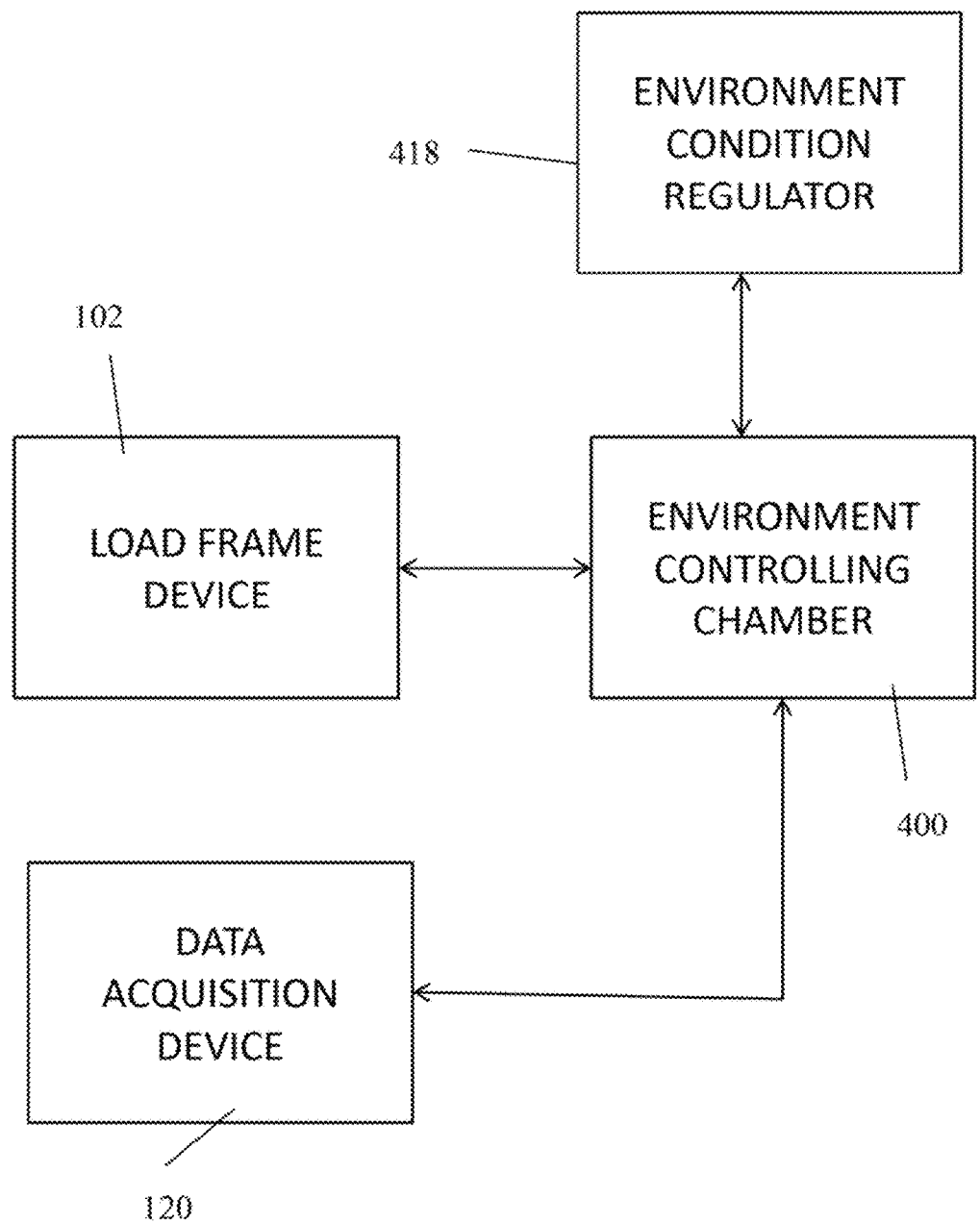
FIG. 8 is bloc diagram illustrating the connection between a load frame device, an environment controlling chamber and an environment condition regulator, a data acquisition device and a load monitoring device according to an embodiment of the present invention.

FIG. 8 illustrates the connection between the load frame device 102, the environment controlling chamber 400, the environment condition regulator 418 and the data acquisition device 120 in accordance with an embodiment of the invention. the data acquisition device 120 is further adapted t be connected to the load monitoring system 130 in accordance with an embodiment of the invention.

Accordingly, many variations of these embodiments are envisaged within the scope of the present invention.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The embodiments were chosen and described in order to best explain the principles of the present invention and its practical application, and to thereby enable others skilled in the art to best utilize the present invention and various embodiments with various modifications as are suited to the particular use contemplated. It is understood that various omissions and substitutions of equivalents are contemplated as circumstances may suggest or render expedient, but such omissions and substitutions are intended to cover the application or implementation without departing from the spirit or scope of the present invention.

The invention claimed is:

1. A load frame device comprising:
a top plate;
a base plate; and
one or more load testing frames, each one comprising:
a first pair of jaws to hold and secure in place a first portion of one or more test specimens;
a load cell to be securely seated and coupled to the base plate; and
a second pair of jaws to be connected to the load cell such that the force applied on the second pair of jaws is transferred to the load cell for measurement wherein, the load frame device further comprises one or more environment controlling chambers to be positioned within or around the one or more load testing frames,
wherein the one or more environment controlling chambers further comprises:
an input and output opening connected to a conveyor,
a base cover having a base cover opening,
wherein the input and output opening enables the entry and exit of a substance through the one or more environment controlling chambers,
wherein the substance is liquid or gas;
a top cover having a top cover opening,
wherein the base cover opening and the top cover opening receives the one or more test specimens such that, an intermediary portion of the one or more test specimens is positioned inside the one or more environment controlling chambers; and
wherein the load frame device receives and tests simultaneously, but independently, at least two test specimens.

2. The load frame device as claimed in claim 1, wherein the one or more load testing frames comprise two testing frames.

3. The load frame device as claimed in claim 1, further comprising:
a first sub-frame structure which tests a first test specimen, and
a second sub-frame structure which tests a second test specimen,
wherein the first sub-frame structure is independent of the second sub-frame structure.

4. The load frame device as claimed in claim 1, wherein the one or more environment controlling chambers have the same or different environment conditions.

5. The load frame device as claimed in claim 4 further comprising:
one or more environment condition regulators to be connected to the one or more environment controlling chambers for regulating desired environmental conditions within the one or more environment controlling chambers, wherein the one or more environment controlling chambers receive the one or more test specimens.

6. The load frame device as claimed in claim 5, wherein the one or more test specimens comprise two test specimens.

7. The load frame device as claimed in claim 5, wherein the one or more environment controlling chambers comprises one or more heaters.

8. The load frame device as claimed in claim 7, wherein the one or more heaters are located inside or outside of the one or more environment controlling chambers.

9. The load frame device as claimed in claim 4, wherein the one or more environment controlling chambers is a hermetically sealed chamber and receives the one or more test specimens.

10. The load frame device as claimed in claim 4, wherein the one or more environment controlling chambers receive liquid and gas substances for testing the one or more test specimens.

11. The load frame device as claimed in claim 4, wherein the one or more environment controlling chambers is made of a composite material or PMMA material.

12. The load frame device as claimed in claim 4, wherein:
a first environment controlling chamber is used for a first test specimen;
a second environment controlling chamber is used for a second test specimen; and
the first and second test specimens are subject to different environmental conditions imposed by the first and second environment controlling chambers, respectively.

13. The load frame device as claimed in claim 1, wherein the load frame device is connected to a data acquisition device for:
receiving electrical signals of sustain load measurements of the one or more test specimens, converting the received electrical signals into digital signals, and
transmitting the digital signals representing the sustain load measurements to a load monitoring device.

14. The load frame device as claimed in claim 13, wherein the load monitoring device comprises a microprocessor for: receiving and monitoring the sustain load measurements of the one or more test specimens; and storing the sustain load measurements inside a memory.

15. The load frame device as claimed in claim 1, further comprising one or more environment controlling chambers which comprises sensors connected to a data acquisition device, wherein the sensors detect and transmit environment conditions within the one or more environment controlling chambers, and wherein the data acquisition device reads the environment conditions from the sensors in real time.

16. The load frame device as claimed in claim 1, wherein the one or more load testing frames further comprises:
a pair of pillars supported at one end by the top plate;
a crosshead to be mounted and to move along the pair of pillars;
a power screw to be in physical contact with the crosshead through an opening in the top plate for applying a force thereon for engaging the first pair of jaws to move along the pair of pillars;
wherein the power screw engages a force on the cross head for moving the cross head depending on a load desired; and
wherein the first pair of jaws is coupled to the crosshead.

17. A load frame device comprising:
a top plate;
a base plate;
one or more load testing frames, each one comprising:
a pair of pillars supported at one end by the top plate;
a crosshead to be mounted and to move along the pair of pillars;
a first pair of jaws to be coupled to the crosshead and to hold and secure in place a first portion of one or more test specimens;
a power screw to be in physical contact with the crosshead through an opening in the top plate for applying a force thereon for engaging the first pair of jaws to move along the pair of pillars, wherein the power screw engages a force on the cross head for moving the cross head depending on a load desired;
a load cell to be securely seated and coupled to the base plate; and
a second pair of jaws to be connected to the load cell such that the force applied on the second pair of jaws is transferred to the load cell for measurement,
wherein the load frame device receives and tests simultaneously, but independently, at least two test specimens.

18. A load frame device comprising:
a top plate;
a base plate;
one or more load testing frames, each one comprising:
a pair of pillars supported at one end by the top plate;
a crosshead to be mounted and to move along the pair of pillars;
a first pair of jaws to be coupled to the crosshead and to hold and secure in place a first portion of one or more test specimens;
a power screw to be in physical contact with the crosshead through an opening in the top plate for applying a force thereon for engaging the first pair of jaws to move along the pair of pillars, wherein the power screw engages a force on the cross head for moving the cross head depending on a load desired;
a load cell to be securely seated and coupled to the base plate;
a second pair of jaws to be connected to the load cell such that the force applied on the second pair of jaws is transferred to the load cell for measurement; and
one or more environment controlling chambers which comprises sensors connected to a data acquisition device, wherein the sensors detect and transmit environment conditions within the one or more environment controlling chambers, and wherein the data acquisition device reads the environment conditions from the sensors in real time.

* * * * *